United States Patent [19]
Gamble et al.

[11] Patent Number: 5,576,456
[45] Date of Patent: Nov. 19, 1996

[54] RECOVERY OF COMPONENTS FROM POLYESTER RESINS

[75] Inventors: William J. Gamble, Rochester; Andrius A. Naujokas, Webster, both of N.Y.

[73] Assignee: Eastman Kodak Company, Rochester, N.Y.

[21] Appl. No.: 589,444

[22] Filed: Jan. 22, 1996

[51] Int. Cl.[6] .................................................. C07C 67/60
[52] U.S. Cl. .......................... 560/78; 562/483; 562/485; 568/854; 521/48.5; 528/481; 528/496
[58] Field of Search .............................. 560/78; 562/483, 562/485; 568/854; 521/48.5; 528/481, 496

[56] References Cited

U.S. PATENT DOCUMENTS

| | | | |
|---|---|---|---|
| 3,907,868 | 9/1975 | Currie et al. | 260/475 |
| 5,051,528 | 9/1991 | Naujokas et al. | 560/78 |
| 5,298,530 | 3/1994 | Gamble et al. | 521/48.5 |
| 5,414,022 | 5/1995 | Toot, Jr. et al. | 521/48 |
| 5,432,203 | 7/1995 | DeBruin et al. | 521/48.5 |

*Primary Examiner*—Samuel Barts
*Attorney, Agent, or Firm*—Joshua G. Levitt

[57] ABSTRACT

There is described a process for the depolymerization of polyethylene terephthalate into component monomers using a reactor in which the polyethylene terephthalate is a discontinuous phase which contacts a continuous phase of superheated methanol vapor.

8 Claims, 1 Drawing Sheet

RECOVERY OF COMPONENTS FROM POLYESTER RESINS

FIELD OF THE INVENTION

This invention relates to a process for recovering ester and glycol components from condensation-type polyester resins and to apparatus for carrying out that process.

BACKGROUND OF THE INVENTION

Polyester resins have found widespread use in varied applications. Polyesters such as polyethylene terephthalate are used in photographic film, in magnetic tape, in fibers, and in food and beverage containers. Various methods have been disclosed for the depolymerization of such resins into their component monomers, such as ethylene glycol and terephthalic acid or derivatives thereof, so that they can be reused.

Some of these methods are described in such patents as U.S. Pat. Nos. 3,037,050, 3,321,510, 3,884,850, 3,907,868, 4,163,860, 4,578,502, 4,620,032, 4,876,378 and 5,095,145, and in European Published Patent Application 0 484 963 published May 13, 1992.

A particularly useful technique for recovering scrap polyester is described in a series of patent that begins with Naujokas et al. U.S. Pat. No. 5,051,528. This patent describes a process of recovering ethylene glycol and dimethyl terephthalate from polyethylene terephthalate scrap resins by dissolving the polyester resin in oligomers of the same monomers as are present in the polyester, passing super-heated methanol through the solution and recovering ethylene glycol and dimethyl terephthalate.

Gamble et al. U.S. Pat. No. 5,298,530, issued Mar. 29, 1994 improves on the process of the '528 patent by combining scrap resin with reactor melt in a dissolver before the dissolver melt is transferred to the reactor for contact with super-heated methanol. In the reactor, polymers and oligomers are further depolymerized into the component glycol and ester monomers, which are then recovered.

Toot et al. U.S. Pat. No. 5,414,022, issued May 9, 1995, optimizes the conditions of the processes of Naujokas et al. and Gamble et al., cited above.

DeBruin et al U.S. Pat. No. 5,432,203, issued Jul. 11, 1995, extends the processes of prior patents in the series to convert ethylene glycol and dimethyl terephthalate to bishydroxyethyl terephthalate, which then can be used as feedstock for the formation of polyethylene terephthalate.

The processes described in this series of patents and applications have numerous advantages. These include low cost, high efficiency, the ability to operate at relatively low pressure and the ability to be used with a variety of forms of polyester of varying degrees of cleanliness and purity.

The processes and equipment described in this series of patents and applications employ a reactor in which a discontinuous phase of superheated methanol is passed through a continuous phase of molten polyester and polyester decomposition products. While such a reactor is useful, we have found that the conversion rate of polyester to monomer can be improved by the use of a reactor in which the superheated methanol is the continuous phase and molten polyester and polyester decomposition products are the discontinuous phase. We have found that this can be accomplished by using a staged column as the reactor.

SUMMARY OF THE INVENTION

The present invention provides a process for converting polyester to its component monomers. The apparatus used to carry out the process of the present invention is similar to that used for the process described in U.S. Pat. No. 5,298, 530. One significant difference is that it employs as the reactor in which the bulk of the conversion takes place a staged column in which methanol vapor is the continuous phase and the molten polyester and polyester decomposition products is the discontinuous phase.

Thus, the present invention is a process for depolymerizing polyester into its components using apparatus that comprises:

a dissolver for receiving polyester and a staged column reactor for depolymerizing polyester into monomer components and for separating monomer components from higher boiling materials, the process comprising the steps of:

a) forming a melt of polyester in the dissolver, b) passing super-heated methanol through the reactor to form a continuous phase of methanol vapor in the reactor, c) transferring polyester from the dissolver to the reactor to form a discontinuous phase which contacts the methanol vapor to depolymerize the polyester into component monomers which are removed from the reactor by the methanol vapor, d) removing higher molecular weight materials from the reactor as a liquid phase, and e) removing methanol and component monomers from the reactor as a vapor phase.

In a preferred embodiment, the polyester added to the dissolver is combined with liquid from the reactor and the two are retained in the dissolver for a period of time sufficient to initiate depolymerization of the polyester and provide reduced chain length polyester.

While a staged column reactor is shown in the polyester recovery process described in Currie et al. U.S. Pat. No. 3,907,868, that reactor is operated in such a way that methanol is the discontinuous phase, as it is in the other recovery processes of which we are aware.

DETAILED DESCRIPTION OF THE INVENTION

Figure 1:
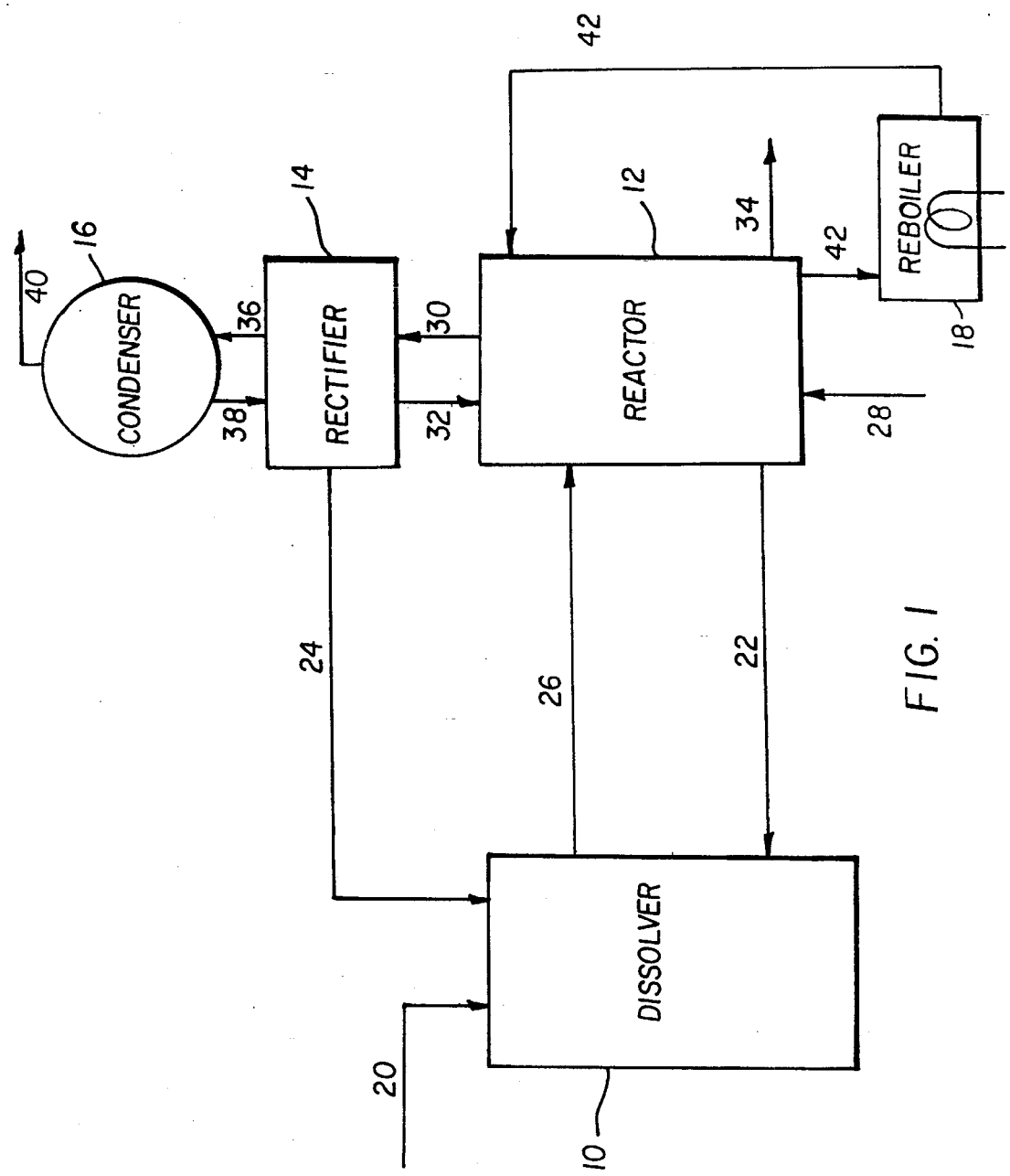
FIG. 1 is a schematic flow diagram illustrating the inventive process and apparatus utilizing a staged countercurrent reactor.

FIG. 1 schematically illustrates apparatus to carry out a preferred embodiment of the process of the invention.

In the apparatus shown in FIG. 1 a dissolver (10), a reactor (12), a rectifier (14) and a condenser (16) are connected by the pipes, pumps and valves needed to transfer the reactants from one location to another in accordance with the reaction.

Polyethylene terephthalate (20) in a suitable form and size is introduced into the dissolver by any suitable means where it is liquefied and reduced in chain length. The dissolver can be run at atmospheric pressure, or slightly positive or negative pressure, and is equipped with means for heating its contents to a temperature of up to about 305° C. The dissolver preferably is maintained at a temperature in the range of 240° to 260° C.

Reactor melt (22), and optionally rectifier liquid (24), are introduced into the dissolver via means that can be used to control the rate of introduction of these materials and their relative proportions. Reactor melt, and optional rectifier liquid, introduced into the dissolver react with the polyester to shorten the average chain length. This initiates the depolymerization reaction and decreases the viscosity of the dissolver contents. There can be added to the dissolver an ester exchange catalyst, such as zinc acetate. Preferably the catalyst is employed in the range of 30 to 300 ppm polyester, and most preferably the catalyst is employed in the range of 30 to 100 ppm polyester.

There also can be added to the dissolver sufficient base to neutralize any acid formed from contaminants that may be carried into the dissolver with the polyester scrap. If used, sufficient base is added to maintain the pH equivalent of the melt in the range of 7 to 10; preferably 7 to 8.

In a preferred embodiment, the melt in the dissolver is protected from the atmosphere by a blanket of inert gas, such as nitrogen, carbon dioxide, argon, etc. This reduces degradation of the dissolver melt due to oxidation reactions.

The reactor and dissolver melts comprise methanol, low molecular weight polyesters, monomers, monohydric alcohol-ended oligomers, glycols, and dimethylterephthalate and methylhydroxyethyl terephthalate. The major difference between these two melts is the average chain length of the polyester. The rectifier liquid contains the same components except for polyesters.

The viscosity of the dissolver melt preferably is maintained in the range of 0.002 to 0.1 Pa.s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

Low boiling components which evolve in the dissolver may contain monomers that can be recovered together with the monomers exiting the reactor. This can be accomplished by, in separate apparatus, absorbing them into by liquid methanol and recovering them in a separate process.

Melt (26) from the dissolver is transferred to the reactor where it will constitute a discontinuous phase. It typically will be added toward the top of the reactor and will flow toward the bottom of the reactor by gravity. There will be added toward the bottom of the reactor sufficient super heated methanol vapor (28) to fill the column and form a continuous vapor phase in the reactor thorough which the polyester melt descends.

The reactor can comprise packing or trays over which the melt is distributed, thereby increasing the surface area of melt that can come in contact with the methanol vapor. The increased contact area in such reactors facilitates the depolymerization reaction. While a packed column reactor is preferred because of economy of operation, a thin film or wiped film reactor can be employed and still obtain the operational advantages of this invention.

The column is run under conditions that will maintain the methanol vapor as the continuous phase and will have sufficient stages for the depolymerization reaction to be essentially completed in the reactor. Typically it will have from 3 to 20 ideal stages and preferably will have 5 to 8 ideal stages. Conditions for operating the reactor to maintain the methanol vapor as the continuous phase are a temperature in the range of 240° to 300° C. and a pressure from atmospheric to slightly elevated pressure up to about 300 kPaa.

The super-heated methanol vapor can be provided to the reactor by conventional means. Methanol is introduced into the reactor at a rate in the range of 2 to 6 parts by weight methanol per part polyester.

There can transferred from the reactor to a separate rectifier a vapor stream (30) comprising methanol, dimethylterephthalate, glycols including ethylene glycol, diethylene glycol, and triethylene glycol, dimethylisophthalate, cyclohexanedimethanol, and methylhydroxyethyl terephthalate. The rectifier separates higher boiling components, such as methylhydroxyethyl terephthalate, from the vapor stream exiting the reactor and returns it to the reactor in the form of a liquid (32). Part or all of this liquid (24) can be sent to the dissolver to adjust viscosity. While the rectifier is shown as a separate apparatus, it can comprise stages of the depolymerization reactor (12) above the point at which dissolver melt is added.

The vapor stream (36) exiting the rectifier is passed to a reflux condenser where higher boiling components (38) are returned to the reactor and the vapor phase (40) is sent for recovery. The condenser is operated at a temperature in the range of 165° to 210° C. and at atmospheric to slightly elevated pressure, up to about 300 kPaa.

Exiting the condenser is a vapor stream (40) which comprises, methanol, ethylene glycol and dimethyl terephthalate. These components are separated from one another and purified in subsequent operations.

There is removed from the base of the reactor high boiling impurities and reaction by-products (34). Depending on the specific composition of this stream, it can be discarded or sent for recovery of specific components.

At the bottom of the reactor there can optionally be located a reboiler (18) which provides energy to the reactor. Melt (42) can be withdrawn toward the bottom of the column, heated and reintroduced toward the top of the column. Use of such a reboiler to heat the contents of the reactor permits adjusting the operation of the column without being dependent on a minimum amount of melt being introduced from the dissolver.

The invention has been described by reference to preferred embodiments, but it will be understood changes can be made to the apparatus and process steps specifically described herein within the spirit and scope of the invention.

What is claimed is:

1. A process for depolymerizing polyester into its components using apparatus that comprises:

a dissolver for receiving polyester and a staged column reactor for depolymerizing polyester into monomer components and for separating monomer components from higher boiling materials, the process comprising the steps of:

a) adding polyester to the dissolver and combining it with liquid from the reactor to form a melt of reduced chain length polyester, b) passing super-heated methanol through the reactor to form a continuous phase of methanol vapor in the reactor, c) transferring reduced chain length polyester from the dissolver to the reactor to form a discontinuous phase which contacts the methanol vapor to depolymerize the polyester into component monomers which exit the reactor with the methanol vapor, d) removing higher molecular weight materials from the reactor as a liquid phase, and e) removing methanol and component monomers from the reactor as a vapor phase.

2. A process of claim 1, wherein the staged column reactor has 3 to 20 ideal stages.

3. A process of claim 1, wherein the staged column reactor has 5 to 8 ideal stages.

4. A process of claim 1, wherein the staged column reactor is operated at a temperature in the range of 240° to 300° C. and a pressure from atmospheric to 300 kPaa.

5. A process of claim 1, wherein methanol vapor is added to the bottom of the reactor in an amount in the range of 2 to 6 parts by weight based on the weight of the melt added to the top of the reactor from the dissolver.

6. A process of claim 1, wherein the reactor comprises a packed column.

7. A process of claim 1, wherein the reactor comprises a trayed column.

8. A process of claim 1, wherein a reboiler is present at the bottom of the reactor through which melt is circulated, heated and returned to the top of the reactor.

* * * * *